United States Patent
Tchaplinski et al.

(10) Patent No.: US 9,670,145 B2
(45) Date of Patent: Jun. 6, 2017

(54) PROCESS FOR PREPARING 1,1-DISUBSTITUTED ETHYLENE MONOMERS

(71) Applicant: AFINITICA TECHNOLOGIES, S. L., Cerdanyola del Vallès (ES)

(72) Inventors: Vladimir Tchaplinski, Cerdanyola del Vallès (ES); Stefano Gherardi, Cerdanyola del Vallès (ES); Verónica De La Fuente Molina, Cerdanyola del Vallès (ES)

(73) Assignee: AFINITICA TECHNOLOGIES, S. L., Cerdanyola del Vallès (ES)

( * ) Notice: Subject to any disclaimer, the term of this patent is extended or adjusted under 35 U.S.C. 154(b) by 0 days.

(21) Appl. No.: 15/300,988

(22) PCT Filed: Aug. 29, 2014

(86) PCT No.: PCT/IB2014/064144
§ 371 (c)(1),
(2) Date: Sep. 30, 2016

(87) PCT Pub. No.: WO2015/150882
PCT Pub. Date: Oct. 8, 2015

(65) Prior Publication Data
US 2017/0022151 A1    Jan. 26, 2017

(30) Foreign Application Priority Data

Mar. 31, 2014   (EP) .................................... 14382127

(51) Int. Cl.
| | | |
|---|---|---|
| *C07C 253/30* | (2006.01) | |
| *C07D 307/12* | (2006.01) | |
| *C07C 67/343* | (2006.01) | |
| *C07F 7/08* | (2006.01) | |

(52) U.S. Cl.
CPC .......... *C07C 253/30* (2013.01); *C07C 67/343* (2013.01); *C07D 307/12* (2013.01); *C07F 7/0818* (2013.01); *C07C 2101/14* (2013.01); *C07C 2101/16* (2013.01)

(58) Field of Classification Search
CPC .................................................... C07C 253/30
USPC ........................................................ 558/377
See application file for complete search history.

(56) References Cited

U.S. PATENT DOCUMENTS

| | | |
|---|---|---|
| 3,559,652 A | 2/1971 | Banitt et al. |
| 3,654,340 A | 4/1972 | Banitt |
| 3,927,078 A | 12/1975 | Lapporte |
| 3,931,412 A | 1/1976 | Kensler, Jr. et al. |
| 4,100,200 A | 7/1978 | Maggiulli et al. |
| 4,321,180 A | 3/1982 | Kimura et al. |
| 6,245,933 B1 | 6/2001 | Malofsky et al. |
| 6,977,278 B1 | 12/2005 | Misiak |
| 7,718,821 B1 | 5/2010 | Bigi et al. |
| 7,829,730 B2 | 11/2010 | Hiyama et al. |

FOREIGN PATENT DOCUMENTS

| | | |
|---|---|---|
| EP | 0127855 A1 | 12/1984 |
| EP | 0459617 A1 | 12/1991 |
| JP | H06-192202 A | 7/1994 |
| WO | 94/15907 A1 | 7/1994 |
| WO | 96/40695 A1 | 12/1996 |
| WO | 2008/050313 A1 | 5/2008 |
| WO | 2010/129066 A1 | 11/2010 |
| WO | 2013/113037 A1 | 8/2013 |

OTHER PUBLICATIONS

Bugarin A. et al.: "Efficient, direct alfa-methylenation of carbonyls mediated by diisopropylammonium trifluoroacetate", Chemical Communication, vol. 46, Jan. 25, 2010 (Jan. 25, 2010), pp. 1715-1717.
Anniina Erkkilä et al., "Iminium Catalysis", Chem. Rev., 2007, 107 (12), pp. 5416-5470.
International Search Report dated Dec. 11, 2014 from corresponding International Application No. PCT/IB2014/064144; 4 pgs.
S. Ebnesajjad Ed., "Adhesives Technology Handbook", William Andrew Inc., 2008.
Mizrahi et al., Acta Biomater., 2011, 7(8), 3150-3157.
Houben Weyl, vol. 11/12, p. 616 and vol. 2, p. 203, 1967.
V.P. Kukhar et al., Zhurnal Organicheskoi Khimil, 1981, 17(1), 180-6.

*Primary Examiner* — Kristin Vajda
(74) *Attorney, Agent, or Firm* — Maier & Maier, PLLC

(57) ABSTRACT

The present invention relates to a process for preparing 1,1-disubstituted ethylene monomers having general formula (I) from a compound of general formula (II) and an active methylene compound of general formula (III) using a catalytic amount of an ammonium or iminium a salt in homogeneous phase or supported on a solid substrate. Said process allows the direct synthesis of the monomers and finds application in the preparation of a wide variety of monomers. The products obtained are reactive monomers of high purity which find application in the field of fast curing adhesives.

15 Claims, No Drawings

PROCESS FOR PREPARING 1,1-DISUBSTITUTED ETHYLENE MONOMERS

TECHNICAL FIELD

The present invention relates to a process for preparing 1,1-disubstituted ethylene monomers, such as cyanoacrylates or methylidene malonates, which find application in the field of fast curing adhesives.

TECHNICAL BACKGROUND

Cyanoacrylate is the generic name for a family of resistant fast acting adhesives based on esters of 2-cyanoacrylic acid. The structure of the monomer is as follows:

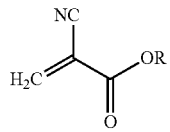

wherein R is generally an alkyl group such as, for example, methyl, ethyl, butyl or 2-octyl.

Such compounds are well known for some time, as disclosed in, for example, the manual S. Ebnesajjad Ed., *Adhesives Technology Handbook*, William Andrew, Norwich, 2008.

These compounds are ethylene monomers 1,1-disubstituted with electron withdrawing groups, so that they olefins are highly reactive towards nucleophiles for its electron deficiency. Their structure allows an extremely easy polymerisation thereof initiated by any nucleophilic or basic species which is inherently present in the medium or substrate to be bonded.

The industrial process for the preparation of cyanoacrylates is based on the well-known Knoevenagel reaction involving the reaction of a cyanoacetate with a source of formaldehyde, for example, paraformaldehyde or trioxane, with an appropriate cyanoacetate in basic medium. Reaction conditions inevitably result in a prepolymer, which must be subjected to a thermal depolymerization at high temperature, high vacuum and acidic conditions. The pure monomers are usually re-distilled and stabilized by trace quantities of acids, to avoid an undesired polymerization. Due to the strong conditions of the depolymerization process, this procedure is not appropriate for monomers that include thermally labile substituents.

In the prior art several improvements to such method have been described, as disclosed, for example, in the U.S. Pat. No. 6,245,933, and the references cited therein.

Despite the improvements introduced, the process based on the Knoevenagel reaction is efficient only for lower alkyl cyanoacrylates, for example, ethyl cyanoacrylate which constitutes nearly more than 90% of the production of cyanoacrylates to be used in fast curing adhesives. In these cases it is possible to implement waste recycling systems that allow obtaining satisfactory yields.

For other cyanoacrylates, the yields obtained by means of the Knoevenagel reaction are substantially low. For example, 2-phenylethyl cyanoacrylate is obtained with 39%, as disclosed in the Japanese patent application JP-A-06-192202; ethyl glycolate cyanoacrylate is obtained with a yield of 23%, as disclosed in the European patent application EP-A-0127855; trimethylsilylmethyl cyanoacrylate with a 30% yield as disclosed in the European patent application EP-A-0459617; tetrahydrofurfuryl cyanoacrylate with a 64% before being distilled, as disclosed in the U.S. Pat. No. 4,321,180; and alkoxyethyl cyanoacrylates with a yield ranging from 14% for hexoxy group, to 45% for the methoxy group, as disclosed in Muzrahi et al., Acta Biomater., 2011, 7(8), 3150-3157.

However, the applicative properties on an adhesive depend largely on the ability to combine in a single formulation different monomers to achieve certain effects, in the same way that different acrylic monomers are combined in a paint to achieve, for example, increased hardness and durability.

Additionally, it should be born in mind that other kind of monomers which polymerize instantaneously, methylidene malonates, which also belong to the class of 1,1-disubstituted ethylene monomers, are difficult to be efficiently obtained by a process based on the Knoevenagel reaction. Improvements of this process are disclosed in the international patent application WO-A-2010/129066.

In the prior art a number of procedures different from the Knoevenagel reaction have been disclosed to obtain cyanoacrylate monomers with improved yield and purity, as well as to expand the range of monomers.

Thus, in the U.S. Pat. No. 3,654,340 it is disclosed the condensation of formaldehyde with a cyanoacetate in the presence of a mixture of an acid and a salt of a primary or secondary amine with the same acid or with a stronger acid. This procedure leads to obtaining a prepolymer, which must be thermally depolymerized to produce the monomer.

In the international patent application WO-A-94/15907 it is disclosed the esterification of 2-cyanoacryloyl chloride with an alcohol or with a diol to obtain biscyanoacrylates. Said process involves several drawbacks such as a fact of using corrosive and moisture sensitive reagents to prepare said acid chloride. Furthermore, the cyanoacrylic acid should be obtained by pyrolysis of an ester, probably obtained from the Knoevenagel reaction.

In the international patent application WO-A-2008/050313 a process for the preparation of electron deficient olefins is disclosed, wherein some specific iminium salts are used, called ionic liquids, in stoichiometric amounts, as the iminium salt is the carrier of the methylidene group of the cyanoacrylate. In said process the monomer is directly obtained by reaction of the iminium salt with a cyanoacetate, so the thermal depolymerization is avoided, but it has the disadvantage that the ammonium salt, derived from the iminium salt, remains as a residue after the distillation and it must be recovered and treated to regenerate the amine to subsequently obtain the corresponding iminium salt.

In the U.S. Pat. No. 7,718,821 a method for the preparation of electron-deficient olefins such as a cyanoacrylate is disclosed, wherein an iminium salt is used in a stoichiometric amount, since said salt provides the methylidene group of the cyanoacrylate. Such iminium salt is obtained by reaction between an aldehyde and a primary amine, and subsequent protonation with an acid. When an unprotonated iminium salt is employed, such as the iodide Eschenmoser's salt (N,N-dimethylmethylideneammonium iodide), the reaction proceeds in a low yield. In said process the monomer is also obtained directly by reaction of the protonated iminium salt with a cyanoacetate, so that the thermal depolymerization is avoided. However, the residue cannot be directly reused and the ammonium salt thus obtained must be treated to regenerate the amine and this, in turn, form the corresponding iminium salt by reaction with paraformaldehyde. This problem of the residual by-product is further aggravated when the iminium salt is used in excess relative to the cyanoacetate, as disclosed, for example, in the International Patent Application WO-A-2013/113037.

Thus, there remains a need to provide an alternative process for the preparation of 1,1-disubstituted ethylene monomers that allows the direct preparation of such monomers from simple, readily available and non-toxic starting products, and that is applicable to a wide range of monomers.

OBJECT OF THE INVENTION

The object of the present invention is a process for preparing 1,1-disubstituted ethylene monomers.

DETAILED DESCRIPTION OF THE INVENTION

The object of the present invention is a process for preparing 1,1-disubstituted ethylene monomers of general formula (I)

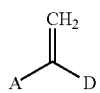

(I)

wherein:
A and D are independently selected from each other from the functional groups CN, $CO_2R^1$, $COR^1$, $CONR^1_2$, $SO_2R^1$, $SO_3R^1$, $COPO(OR^1)_2$, $COPOR^1_2$, $NO_2$, wherein $R^1$ means a linear or branched, saturated or unsaturated $C_1$-$C_{20}$ alkyl, preferably linear, branched or alicyclic $C_1$-$C_3$ alkyl, or linear, branched or alicyclic $C_4$-$C_{20}$ alkyl, $C_1$-$C_{20}$ halogenated alkyl, $C_4$-$C_{20}$ alkyl silane, $C_1$-$C_{20}$ acetoxy silane, $C_2$-$C_{20}$ alkoxyalkyl, $C_2$-$C_{20}$ alkenyl, $C_2$-$C_{20}$ alkynyl, $C_2$-$C_{10}$ alkylene, $C_3$-$C_{20}$ cycloalkyl, alkylcycloalkyl, $C_3$-$C_{20}$ cycloalkenyl, alkylcycloalkenyl, aryl, substituted aryl, alkylaryl, substituted alkylaryl, aliphatic heterocyclic moiety, alkyl moiety linked to an aliphatic heterocycle, aromatic heterocycle moiety, alkyl moiety linked to an aromatic heterocycle, acrylic ester moiety, oxetane moiety, epoxy moiety, glycolate moiety, and carboxylic acid ester moiety;
which comprises the reaction of a compound of general formula (II)

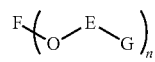

(II)

wherein:
E is $(CH_2X)_m$,
m is comprised between 1 and 20,
X is O or S,
when n=1, F is selected from the functional groups:

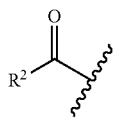

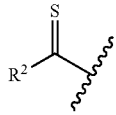

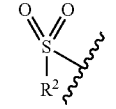

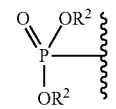

when n=2, F is selected from the functional groups:

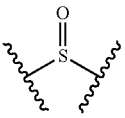

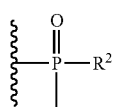

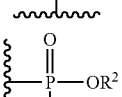

when n=3, F is:

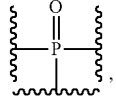

G is selected from the functional groups:

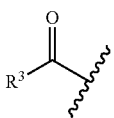 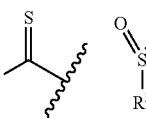 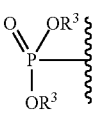

G and F are independently selected from each other, and
$R^2$ and $R^3$ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, or
when n=1, F may be connected to G through one $R^6$ group selected from $(CH_2)_p$, $(CHR')_p$, $(CR'R'')_p$, where p is comprised between 1-6, preferably between 1 and 4, and more preferably is 1, and R' and R'' may be the same or different $C_1$-$C_4$ alkyl groups, with a compound of general formula (III)

(III)

in the presence of a catalytic amount of an ammonium or iminium salt, wherein this salt is in homogeneous phase or supported on a solid substrate, preferably in homogeneous phase.

The authors of the present invention have developed a process for preparing 1,1-disubstituted ethylene monomers that allows the direct preparation of the monomer without the need to include a step of thermal depolymerisation of a prepolymer. In said process simple, readily available and non-toxic starting materials of well-defined structure are used, and it can be applied for the preparation of a wide range of monomers.

Said 1,1-disubstituted ethylene compounds are reactive monomers that find application in the field of fast-curing adhesives. These include cyanoacrylates and methylidene malonates.

The direct synthesis of the monomer, in contrast to the synthesis of a prepolymer that must be thermally depolymerised, is advantageous not only because an energy intensive process is avoided, but also because the thermally sensitive groups which may be present in the ethylene monomer are not subject to aggressive thermal conditions. This, additionally, means that adhesives derived from such compounds have the ability to be thermally activated, if desired.

The process of the invention allows the preparation of monofunctional and polyfunctional monomers irrespective of whether they are liquid or solid, and of a high purity.

In the present description, as well as in the claims, the singular forms "a" or "one" include also the reference to the plural unless the context clearly indicates otherwise.

In this description, the percentages (%) are expressed in weight/weight unless stated otherwise.

Compound of General Formula (I)

The compound of general formula (I)

(I)

is a 1,1-disubstituted ethylene compound, wherein groups A and D are electron withdrawing groups attached to the same carbon atom. Groups A and D may be the same or different, and are independently selected from each other from the functional groups CN, $CO_2R^1$, $COR^1$, $CONR^1_2$, $SO_2R^1$, $SO_3R^1$, $COPO(OR^1)_2$, $COPOR^1_2$, $NO_2$, where $R^1$ means a linear or branched, saturated or unsaturated $C_1$-$C_{20}$ alkyl, preferably linear, branched or alicyclic $C_1$-$C_3$ alkyl, or linear, branched or alicyclic $C_4$-$C_{20}$ alkyl, $C_1$-$C_{20}$ halogenated alkyl, $C_4$-$C_{20}$ alkylated silane, $C_1$-$C_{20}$ acetoxysilane, $C_2$-$C_{20}$ alkoxyalkyl, $C_2$-$C_{20}$ alkenyl, $C_2$-$C_{20}$ alkynyl, $C_2$-$C_{10}$ alkylene, $C_3$-$C_{20}$ cycloalkyl, alkylcycloalkyl, $C_3$-$C_{20}$ cycloalkenyl, alkylcycloalkenyl, aryl, substituted aryl, alkylaryl, substituted alkylaryl, aliphatic heterocycle moiety, alkyl moiety linked to an aliphatic heterocycle, aromatic heterocycle moiety, alkyl moiety linked to an aromatic heterocycle, acrylic ester moiety, oxetane moiety, epoxy moiety, glycolate moiety, and carboxylic acid ester moiety; preferably selected from CN, $CO_2R^1$, $COR^1$, $CONR^1_2$, $SO_2R^1$, and $SO_3R^1$; and more preferably from CN, $CO_2R^1$, and $COR^1$, and still more preferably from CN and $CO_2R^1$. Preferably $R^1$ means a linear or branched, saturated or unsaturated $C_1$-$C_{20}$ alkyl, more preferably linear, branched or alicyclic $C_1$-$C_3$ alkyl, or linear, branched or alicyclic $C_4$-$C_{20}$ alkyl, $C_2$-$C_{20}$ alkoxyalkyl, $C_2$-$C_{20}$ alkenyl, $C_2$-$C_{20}$ alkynyl, $C_2$-$C_{10}$ alkylene, $C_3$-$C_{20}$ cycloalkyl, alkylcycloalkyl, $C_3$-$C_{20}$ cycloalkenyl, alkylcycloalkenyl, aryl, substituted aryl, alkylaryl, substituted alkylaryl, aliphatic heterocycle moiety, alkyl moiety linked to an aliphatic heterocycle, aromatic heterocycle moiety, alkyl moiety linked to an aromatic heterocycle, acrylic ester moiety, and carboxylic acid ester moiety; more preferably $R^1$ means a linear or branched, saturated or unsaturated $C_1$-$C_{20}$ alkyl, more preferably linear, branched or alicyclic $C_1$-$C_3$ alkyl, or linear, branched or alicyclic $C_4$-$C_{20}$ alkyl, $C_2$-$C_{20}$ alkoxyalkyl, $C_2$-$C_{10}$ alkylene, or acrylic ester moiety. In a particularly preferred embodiment, $R^1$ means linear, branched or alicyclic $C_1$-$C_3$ alkyl, such as, for example, methyl, ethyl, n-propyl, i-propyl, or cyclopropyl. In another particularly preferred embodiment $R^1$ means linear, branched or alicyclic $C_4$-$C_{20}$ alkyl, such as, for example, n-butyl, i-butyl, sec-butyl, cyclobutyl, n-hexyl, cyclohexyl, 2-octyl, 2-ethylhexyl, hexadecyl, or stearyl. In another particularly preferred embodiment $R^1$ means $C_2$-$C_{20}$ alkoxyalkyl, such as for example, 2-methoxyethyl, 2-ethoxyethyl, 2-butoxyethyl, 2-isopropoxyethyl, 2-methoxypropyl, or 2-(1-methoxy)propyl. In another particularly preferred embodiment $R^1$ means an acrylic ester moiety.

In a still more preferred embodiment A means CN, D means $COOR^1$, and $R^1$ means linear, branched or alicyclic $C_1$-$C_3$ alkyl. In another still more preferred embodiment A means CN, D means $COOR^1$, and $R^1$ means linear, branched or alicyclic $C_4$-$C_{20}$ alkyl. In another still more preferred embodiment A means CN, D means $COOR^1$, and $R^1$ means $C_2$-$C_{20}$ alkoxyalkyl. In another still more preferred embodiment A means CN, D means $COOR^1$, and $R^1$ means an acrylic ester moiety.

Among the preferred compounds of formula (I), the ones listed in Table I can be mentioned:

TABLE I

| Name | Structure |
|---|---|
| Vinylidene dicyanide | 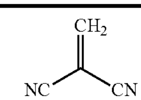 |
| Alkyl cyanoacrylate | 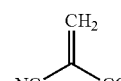 |
| Alkyl methylidene malonates | 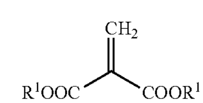 |
| Methylidene diketone | 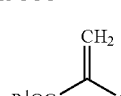 |
| Methylidene β-ketoester | 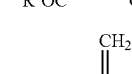 |

When in the compound of formula (I) there are more than one $R^1$ group, these may be the same or different. Halogenated alkyl group may be partially or fully halogenated, and the carbon chain may be linear or branched, as disclosed, for example, in the U.S. Pat. No. 3,654,340. The alkylated silane group may be methyl trimethylsilane, ethyl trimethylsilane, or propyl trimethylsilane, as described, for example, in the European patent application EP-A-0459617. The $C_2$-$C_{20}$ alkoxyalkyl group may be 2-methoxyethyl or 2-ethoxyethyl, as described, for example, in Mizrahi et al., Acta Biomater., 2011, 7(8), 3150-3157. It may be also 2-butoxyethyl, 2-isopropoxyethyl, 2-methoxypropyl, or 2-(1-methoxy)propyl as described, for example, in the U.S. Pat. Nos. 3,559,652, 4,321,180, and 6,977,278. Preferably the $C_2$-$C_{20}$ alkoxyalkyl group is 2-methoxyethyl, 2-ethoxyethyl, 2-butoxyethyl, 2-isopropoxyethyl, 2-methoxypropyl, or 2-(1-methoxy)propyl, more preferably is 2-methoxyethyl, 2-ethoxyethyl, or 2-(1-methoxy)propyl. The allyl and propenyl groups are examples of alkenyl groups, whereas propargyl group is an example of an alkynyl group. Among cycloalkyls, cyclobutyl, cyclohexyl, cycloheptyl or cyclooctyl groups may be mentioned, and among cycloalkenyls, the cyclohexenyl group. Among aliphatic heterocycles, tetrahydrofuryl or tetrahydrothiophene groups may be mentioned, and among aromatic heterocycles, the furyl or thiophenyl groups. When $R_1$ means an acrylic ester moiety is meant to be a group of formula (IV):

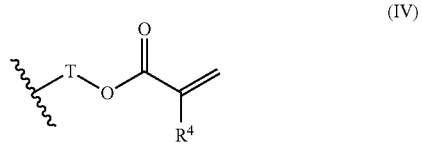

(IV)

wherein T is: $(CH_2)_z$, wherein z is comprised between 2 and 12, preferably between 2 and 8, and more preferably 2 and 6; a branched $C_3$-$C_{12}$, preferably $C_3$-$C_8$, and more preferably $C_3$-$C_6$ alkyl chain; cyclohexylene; optionally substituted biphenylene; optionally substituted —$C_6H_4C(Me)_2C_6H_4$—; optionally substituted —$C_6H_4CH_2C_6H_4$—; or optionally substituted phenylene, and $R^4$ is H, Me, CN or $CO_2R^5$, wherein $R^5$ is a $C_1$-$C_{10}$ alkyl group. When $R^4$ is H or Me, it corresponds to an acrylate or methacrylate moiety respectively. When $R^4$ is CN it corresponds to a cyanoacrylate moiety. When $R^4$ is $CO_2R^5$ it corresponds to a methylidene malonate ester moiety. The glycolate moiety is defined by the formula —$CH_2CO_2R^6$, wherein $R^6$ is a $C_1$-$C_4$ alkyl group. The carboxylic acid ester moiety is defined by the formula —$(CH_2)_kCO_2R^6$, and k is comprised between 2 and 18, preferably between 2 and 12, and more preferably between 2 and 8, and $R^6$ is a $C_1$-$C_4$ alkyl group. In a preferred embodiment A means CN, D means $COOR^1$, $R^1$ means an acrylic ester moiety of formula (IV), wherein $R^4$ means CN, and T means: $(CH_2)_z$, wherein z is comprised between 2 and 12, preferably between 2 and 8, and more preferably 2 and 6; $C_3$-$C_{12}$ branched alkyl chain preferably $C_3$-$C_8$, and more preferably $C_3$-$C_6$; cyclohexylene; optionally substituted biphenylene; optionally substituted —$C_6H_4C(Me)_2C_6H_4$—; optionally substituted —$C_6H_4CH_2C_6H_4$—; or optionally substituted phenylene. In another preferred embodiment A means CN, D means $COOR^1$, $R^1$ means an acrylic ester moiety of formula (IV), wherein $R^4$ means H or Me, and T means: $(CH_2)_z$, wherein z is comprised between 2 and 18, preferably between 2 and 16, and more preferably between 2 and 12; $C_3$-$C_{18}$ branched alkyl chain, preferably $C_3$-$C_{16}$, and more preferably $C_3$-$C_{12}$; cyclohexylene; optionally substituted biphenylene; optionally substituted —$C_6H_4C(Me)_2C_6H_4$—; optionally substituted —$C_6H_4CH_2C_6H_4$—; or optionally substituted phenylene.

Compound of General Formula (II)

The compound of general formula (II)

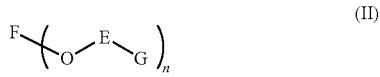

(II)

wherein:
E is $(CH_2X)_m$,
m is comprised between 1 and 20,
X is O or S,
when n=1, F is selected from the functional groups:

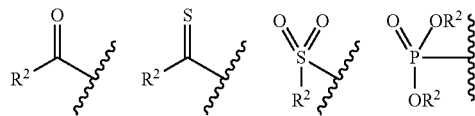

when n=2, F is selected from the functional groups:

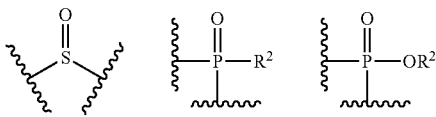

when n=3, F is:

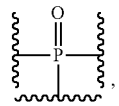

G is selected from the functional groups:

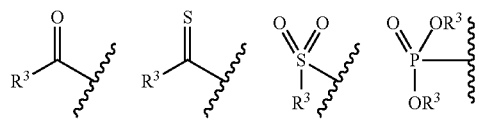

G and F are independently selected from each other, and $R^2$ and $R^3$ are independently selected from each other from the functional groups H, linear or branched $C_1$-$C_4$ alkyl, lineal or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, or when n=1, F may be connected to G through a $R^6$ group selected from $(CH_2)_p$, $(CHR')_p$, $(CR'R'')_p$, where p is comprised between 1-6, preferably between 1 and 4, and more preferably is 1, and R' and R'' may be the same or different $C_1$-$C_4$ alkyl groups, is the compound that provides the methylidene group to the compound of general formula (III).

Preferably E is $(CH_2X)_m$, m is comprised between 1 and 10, X is O or S, n=1, F is selected from the functional groups:

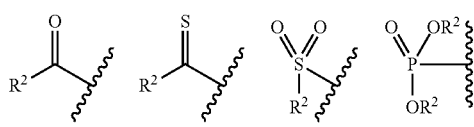

G is selected from the functional groups:

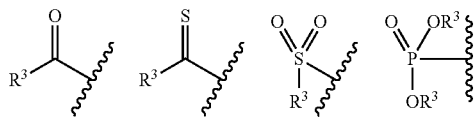

G and F are independently selected from each other, and R² and R³ are independently selected from each other from the functional groups H, linear or branched $C_1$-$C_4$ alkyl, lineal or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, or when n=1, F may be connected to G through a $R^6$ group selected from $(CH_2)_p$, $(CHR')_p$, $(CR'R'')_p$, where p is comprised between 1-6, preferably between 1 and 4, and more preferably is 1, and R' and R'' may be the same or different $C_1$-$C_4$ alkyl groups.

More preferably E is $(CH_2X)_m$, m is comprised between 1 and 5, X is O, n=1, F is selected from the functional groups:

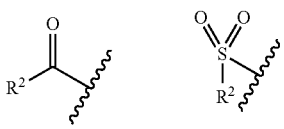

G is selected from the functional groups:

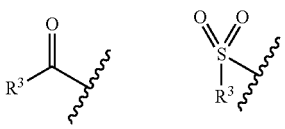

G and F are independently selected from each other, and R² and R³ are independently selected from each other from the functional groups H, linear or branched $C_1$-$C_4$ alkyl, lineal or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, preferably R² and R³ are independently selected from each other from the functional groups H and linear or branched $C_1$-$C_4$ alkyl.

Still more preferably, E is $(CH_2X)_m$, m is comprised between 1 and 3, X is O, n=1, F is:

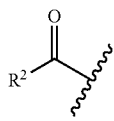

G is:

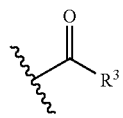

G and F are independently selected from each other, and R² and R³ are independently selected from each other from the functional groups H, linear or branched $C_1$-$C_4$ alkyl, lineal or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, preferably R² and R³ are independently selected from each other from the functional groups H and linear or branched $C_1$-$C_4$ alkyl.

This type of compound can be obtained, for example, by reaction of formaldehyde gas or a source of formaldehyde, such as paraformaldehyde or trioxane, or a source of thioformaldehyde such as trithiane, with acid anhydrides such as, for example, acetic anhydride, thioacetic anhydride, dithiocarboxylic anhydride, methanesulfonic acid anhydride, succinic anhydride, phthalic anhydride, or tert-butoxycarboxylic acid anhydride.

When X is O (oxygen), and n is 1, the compounds are referred to as methylene carboxylic esters, methylene thiocarboxylic esters, methylene sulfonic esters or methylene phosphoric esters, depending on the groups F and G according to the above definitions. The preparation of methylene carboxylic esters is described, for example, in the U.S. Pat. No. 3,927,078. The preparation of methylene sulfonic esters, where F and G groups are connected to a group $R_6$ selected from $(CH_2)_p$, $(CHR')_p$, $(CR'R'')_p$, where p=1-6 and R' and R'' are the same or different $C_1$-$C_4$ alkyl groups, is described in the U.S. Pat. No. 7,829,730.

When X is O (oxygen) and n is 2, the compounds are referred to as oxybismethylene carboxylic esters, oxybismethylene thiocarboxylic esters, oxybismethylene sulfonic esters, or oxybismethylene phosphoric esters, depending on the groups F and G according to the above definitions. The preparation of polyoxymethylene polycarboxylates is described, for example, in the U.S. Pat. No. 3,219,630. The preparation of oxybismethylene carboxylic esters is described, for example, in the U.S. Pat. Nos. 3,927,078 and 3,931,412. The preparation of oxybismethylene sulfonic esters is described, for example, in the U.S. Pat. No. 4,100,200.

The preparation of trioxymethylene carboxylic esters (X is O and n=3) is described, for example, in the U.S. Pat. No. 3,931,412. The preparation of a tris(acyloxymethylene) phosphoric ester is described in the international patent application WO-A-96/40695.

When X is S (sulfur) and n is 1, the compounds are referred to as methylene sulfide carboxylic esters, methylene sulfide thiocarboxylic esters, methylene sulfide sulfonic esters or methylene sulfide phosphoric esters, depending on the groups F and G according to the above definitions.

Among the compounds of general formula (II), the ones listed in Table II may be preferably mentioned:

TABLE II

| Name | Structure |
| --- | --- |
| Methylene diacetate | ![structure] |

TABLE II-continued

| Name | Structure |
|---|---|
| Oxybismethylene diacetate | Me-C(=O)-O-CH2-O-CH2-O-C(=O)-Me |
| Methylene dipropionate | Me-CH2-C(=O)-O-CH2-O-C(=O)-CH2-Me |
| Oxybismethylene dipropionate | Me-CH2-C(=O)-O-CH2-O-CH2-O-C(=O)-CH2-Me |
| Oxybismethylene benzoate propionate | Ph-C(=O)-O-CH2-O-CH2-O-C(=O)-CH2-Me |
| Oxybismethylene dimesylate | MeO2SO-CH2-O-CH2-OSO2Me |
| (Methylsulfonyloxy)methyl-3-methylbutanoate | Me2CH-CH2-C(=O)-O-CH2-OSO2Me |
| Methylene methanedisulfonate | cyclic O2S-CH2-SO2-O-CH2-O |
| Tris(acetoxymethylene) phosphate | P(=O)(O-CH2-OAc)3 |

As compounds of formula (II) the preferred compounds are methylene diacetate, oxybismethylene diacetate, methylene dipropionate, and oxybismethylene dipropionate, more preferred are the compounds methylene diacetate and oxybismethylene diacetate, and still more preferred is methylene diacetate.

Compound of General Formula (III)

The compound of general formula (III):

wherein A and D are as defined above, is an active methylene compound because A and D are electron-withdrawing groups linked to the same carbon atom.

Groups A and D may be the same or different, and are independently selected from each other from the functional groups CN, $CO_2R^1$, $COR^1$, $CONR^1_2$, $SO_2R^1$, $SO_3R^1$, $COPO(OR^1)_2$, $COPOR^1_2$, $NO_2$, where $R^1$ means a linear or branched, saturated or unsaturated $C_1$-$C_{20}$ alkyl, preferably linear, branched or alicyclic $C_1$-$C_3$ alkyl, or linear, branched or alicyclic $C_4$-$C_{20}$ alkyl, $C_1$-$C_{20}$ halogenated alkyl, $C_4$-$C_{20}$ alkylated silane, $C_1$-$C_{20}$ acetoxysilane, $C_2$-$C_{20}$ alkoxyalkyl, $C_2$-$C_{20}$ alkenyl, $C_2$-$C_{20}$ alkynyl, $C_2$-$C_{10}$ alkylene, $C_3$-$C_{20}$ cycloalkyl, alkylcycloalkyl, $C_3$-$C_{20}$ cycloalkenyl, alkylcycloalkenyl, aryl, substituted aryl, alkylaryl, substituted alkylaryl, aliphatic heterocycle moiety, alkyl moiety linked to an aliphatic heterocycle, aromatic heterocycle moiety, alkyl moiety linked to an aromatic heterocycle, acrylic ester moiety, oxetane moiety, epoxy moiety, glycolate moiety, and carboxylic acid ester moiety; preferably A and D are selected from CN, $CO_2R^1$, $COR^1$, $CONR^1_2$, $SO_2R^1$, and $SO_3R^1$; more preferably from CN, $CO_2R^1$, and $COR^1$, and still more preferably from CN and $CO_2R^1$. Preferably $R^1$ means a linear or branched, saturated or unsaturated $C_1$-$C_{20}$ alkyl, more preferably linear, branched or alicyclic $C_1$-$C_3$ alkyl, or linear, branched or alicyclic $C_4$-$C_{20}$ alkyl, $C_2$-$C_{20}$ alkoxyalkyl, $C_2$-$C_{20}$ alkenyl, $C_2$-$C_{20}$ alkynyl, $C_2$-$C_{10}$ alkylene, $C_3$-$C_{20}$ cycloalkyl, alkylcycloalkyl, $C_3$-$C_{20}$ cycloalkenyl, alkylcycloalkenyl, aryl, substituted aryl, alkylaryl, substituted alkylaryl, aliphatic heterocycle moiety, alkyl moiety linked to an aliphatic heterocycle, aromatic heterocycle moiety, alkyl moiety linked to an aromatic heterocycle, acrylic ester moiety, and carboxylic acid ester moiety; more preferably $R^1$ means a linear or branched, saturated or unsaturated $C_1$-$C_{20}$ alkyl, more preferably linear, branched or alicyclic $C_1$-$C_3$ alkyl, or linear, branched or alicyclic $C_4$-$C_{20}$ alkyl, $C_2$-$C_{20}$ alkoxyalkyl, $C_2$-$C_{20}$ alkenyl, or acrylic ester moiety. In a particularly preferred embodiment, $R^1$ means linear, branched or alicyclic $C_1$-$C_3$ alkyl, such as, for example, methyl, ethyl, n-propyl, i-propyl, or cyclopropyl. In another particularly preferred embodiment $R^1$ means linear, branched or alicyclic $C_4$-$C_{20}$ alkyl, such as, for example, n-butyl, i-butyl, sec-butyl, cyclobutyl, n-hexyl, cyclohexyl, 2-octyl, 2-ethylhexyl, hexadecyl, or stearyl. In another particularly preferred embodiment $R^1$ means $C_2$-$C_{20}$ alkoxyalkyl, such as for example, 2-methoxyethyl, 2-ethoxyethyl, 2-butoxyethyl, 2-isopropoxyethyl, 2-methoxypropyl, or 2-(1-methoxy)propyl. In another particularly preferred embodiment $R^1$ means an acrylic ester moiety.

In a still more preferred embodiment A means CN, D means $COOR^1$, and $R^1$ means linear, branched or alicyclic $C_1$-$C_3$ alkyl. In another still more preferred embodiment A means CN, D means $COOR^1$, and $R^1$ means linear, branched or alicyclic $C_4$-$C_{20}$ alkyl. In another still more preferred embodiment A means CN, D means $COOR^1$, and $R^1$ means $C_2$-$C_{20}$ alkoxyalkyl. In another still more preferred embodiment A means CN, D means $COOR^1$, and $R^1$ means an acrylic ester moiety. By an acrylic ester moiety is meant to be a group of formula (IV):

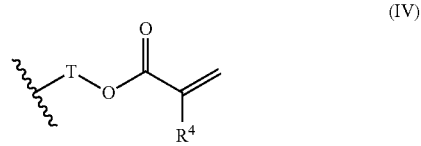

wherein T is: $(CH_2)_z$, wherein z is comprised between 2 and 12, preferably between 2 and 8, and more preferably 2 and 6; a branched $C_3$-$C_{12}$, preferably $C_3$-$C_8$, and more preferably $C_3$-$C_6$ alkyl chain; cyclohexylene; biphenylene optionally substituted; —$C_6H_4C(Me)_2C_6H_4$— optionally substituted; —$C_6H_4CH_2C_6H_4$— optionally substituted; or phenylene optionally substituted, and $R^4$ is H, Me, CN or $CO_2R^5$, wherein $R^5$ is a $C_1$-$C_{10}$ alkyl group. When $R^4$ is H or Me, it corresponds to an acrylate or methacrylate moiety respectively. When $R^4$ is CN it corresponds to a cyanoacrylate moiety. When $R^4$ is $CO_2R^5$ it corresponds to a methylidene malonate ester moiety. The glycolate moiety is defined by the formula —$CH_2CO_2R^6$, wherein $R^6$ is a $C_1$-$C_4$ alkyl group. The carboxylic acid ester moiety is defined by the formula —$(CH_2)_kCO_2R^6$, and k is comprised between 2 and 18, preferably between 2 and 12, and more preferably between 2 and 8, and $R^6$ is a $C_1$-$C_4$ alkyl group. In a preferred embodiment A means CN, D means $COOR^1$, $R^1$ means an acrylic ester moiety of formula (IV), wherein $R^4$ means CN, and T means: $(CH_2)_z$, wherein z is comprised between 2 and 12, preferably between 2 and 8, and more preferably 2 and 6; $C_3$-$C_{12}$ branched alkyl chain preferably $C_3$-$C_8$, and more preferably $C_3$-$C_6$; cyclohexylene; optionally substituted biphenylene; optionally substituted —$C_6H_4C(Me)_2C_6H_4$—; optionally substituted —$C_6H_4CH_2C_6H_4$—; or optionally substituted phenylene. In another preferred embodiment A means CN, D means $COOR^1$, $R^1$ means an acrylic ester moiety of formula (IV), wherein $R^4$ means H or Me, and T means: $(CH_2)_z$, wherein z is comprised between 2 and 18, preferably between 2 and 16, and more preferably between 2 and 12; $C_3$-$C_{18}$ branched alkyl chain, preferably $C_3$-$C_{16}$, and more preferably $C_3$-$C_{12}$; cyclohexylene; optionally substituted biphenylene; optionally substituted —$C_6H_4C(Me)_2C_6H_4$—; optionally substituted —$C_6H_4CH_2C_6H_4$—; or optionally substituted phenylene.

Among the compounds with this structure can be mentioned the following: malononitrile, cyanoacetates, malonates, alkyl acetoacetates, β-diketones, and cyanoacetamides.

Ammonium Salt and Iminium Salt

In the process of the invention, the reaction between the compound of formula (II) and the compound of formula (III) is performed in the presence of a catalytic amount of an ammonium or iminium salt in homogeneous phase, that is, said salt is in the same phase as the reactants, or either said salt is supported on a solid substrate.

Within the context of the invention an ammonium salt means the product resulting from the reaction, for example, of an acid with a primary amine (for example methylamine, ethylamine, ethylenediamine, i-propylamine, aniline, benzylamine), a secondary amine (for example, piperazine, morpholine) or a tertiary amine (for example, N,N'-dimethoxymethylpiperazine), multiple salts being possible in the case that the molecule includes more than one amino group. Preferably the amine is selected from the group consisting of methylamine, piperazine, 2-methylpiperazine, N,N'-dimethoxymethylpiperazine, aniline, benzylamine, 2,6-difluorobenzylamine, trifluoroethylamine, and mixtures thereof; more preferably from piperazine, 2-methylpiperazine and N,N'-dimethoxymethylpiperazine, and still more preferably is piperazine or 2-methylpiperazine.

Within the context of the invention an iminium salt means the imine resulting from the reaction of a primary or secondary amine with an aldehyde or with a ketone, in neutral or acidic medium, which leads to an iminium cation, and that contains an anion from an acid. Preferably an iminium salt resulting from the reaction of a secondary amine with an aldehyde is used, and more preferably with formaldehyde. More preferably the iminium salt is the result of the reaction of N,N-dimethylamine and formaldehyde.

The acid employed for the preparation of the ammonium salt and the iminium salt can be any acid. Preferably the acid is selected from the group consisting of acetic acid, trifluoroacetic acid, sulfuric acid, methanesulfonic acid, p-toluenesulfonic acid, dodecylbenzenesulfonic acid, camphorsulfonic acid, hydrochloric acid, phosphoric acid, and mixtures thereof; preferably the acid is selected from the group consisting of sulfuric acid, methanesulfonic acid, p-toluenesulfonic acid, dodecylbenzenesulfonic acid, and mixtures thereof, and more preferably from methanesulfonic acid, p-toluenesulfonic acid, dodecylbenzenesulfonic acid, and mixtures thereof. It is also possible to employ mixtures of acids and/or mixtures of amines.

In a particularly preferred embodiment the ammonium or iminium salt is the salt formed between an amine selected from the group consisting of piperazine, N,N'-dimethoxymethylpiperazine, and 1,3,5-trimethylhexahydro-1,3,5-triazine, and an acid selected from methanesulfonic acid, p-toluenesulfonic acid, and dodecylbenzenesulfonic acid (LAS).

The preparation of iminium salts is well known to the skilled in the art, since it is well disclosed in the prior art, for example, in the reference manual Houben Weyl, Vol. 11/12, page 616 and Vol 11/2, page 203, as well as in the international patent applications WO-A-2008/050313 and WO-A-2013/113037. They are also commercially available as, for example, Eschenmoser's salt (N,N-dimethylmethylideneammonium iodide, N,N-dimethylmethylideneammonium chloride) through the Sigma-Aldrich company. The anion of said Eschenmoser's salts can be interchanged by means of anion metathesis, as disclosed, for example, in V. P. Kukhar et al., Zhurnal Organicheskoi Khimii, 1981, 17(1), 180-6.

Another procedure for preparing the iminium salt is the reaction between a compound of general formula (II) and an ammonium salt as the product resulting from the reaction between a primary, secondary or tertiary amine and an acid or an acid mixture.

The compound reacting with the ammonium salt is defined by the general formula (II)

wherein:

E is $(CH_2X)_m$, m is comprised between 1 and 20, X is O or S, when n=1, F is selected from the functional groups:

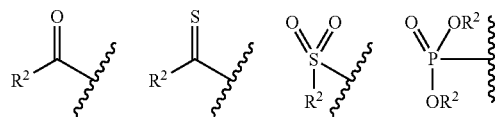

when n=2, F is selected from the functional groups:

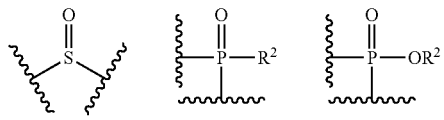

when n=3, F is:

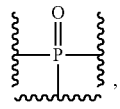

,

G is selected from the functional groups:

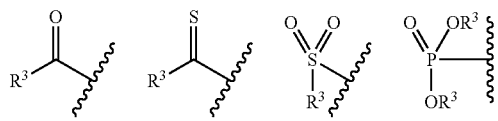

G and F are independently selected from each other, and R² and R³ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, or when n=1, F may be connected to G through one R⁶ group selected from $(CH_2)_p$, $(CHR')_p$, $(CR'R'')_p$, where p is comprised between 1-6, preferably between 1 and 4, and more preferably is 1, and R' and R'' may be the same or different $C_1$-$C_4$ alkyl groups; preferably E is $(CH_2X)_m$, m is comprised between 1 and 10, and X is O or S, n=1, and F is selected from the functional groups:

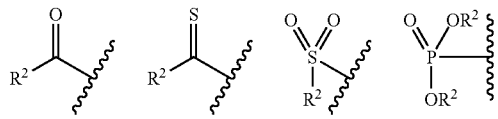

G is selected from the functional groups:

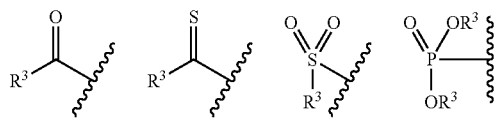

G and F are independently selected from each other, and R² and R³ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, or when n=1, F may be connected to G through one R⁶ group selected from $(CH_2)_p$, $(CHR')_p$, $(CR'R'')_p$, where p is comprised between 1-6, preferably between 1 and 4, and more preferably is 1, and R' and R'' may be the same or different $C_1$-$C_4$ alkyl groups; more preferably E is $(CH_2X)_m$, m is comprised between 1 and 5, and X is O, n=1, and F is selected from the functional groups:

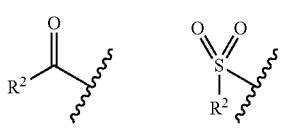

G is selected from the functional groups:

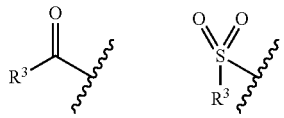

G and F are independently selected from each other, and R² and R³ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, preferably R² and R³ are independently selected from each other from the functional groups H and linear or branched $C_1$-$C_4$ alkyl; still more preferably, E is $(CH_2X)_m$, m is comprised between 1 and 3, X is O, n=1, F is:

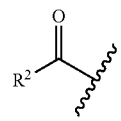

G is:

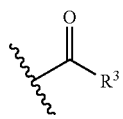

G and F are independently selected from each other, and R² and R³ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, preferably R² and R³ are independently selected from each other from the functional groups H and linear or branched $C_1$-$C_4$ alkyl.

In this process, the reaction is usually carried out at a temperature comprised between 80° C. and 120° C., for a period of time comprised between 5 and 12 hours. The preferred ratio between the compound of general formula (II) and the ammonium salt is comprised between 1.1 and 2. Preferred ammonium salts are those obtained from secondary amines or from the condensation products obtained from these amines and formaldehyde; and more preferably from N,N-dimethylamine, morpholine and N,N,N',N'-tetramethyldiamine methane. Any of the acids mentioned above is suitable for forming the ammonium salt. Preferably it is selected from methanesulfonic acid, p-toluenesulfonic acid, dodecylbenzenesulfonic acid, and mixtures thereof. Preferably the compound of formula (II) is methylene diacetate or oxybismethylene diacetate.

The ammonium salt and the iminium salt can be formed in situ during the execution of the process of the invention, or alternatively can be prepared separately and added independently to the reaction mixture. Preferably, they are prepared in situ.

The ammonium or iminium salt forms part of the same phase as the reactants when it is produced by in situ formation thereof, or else by addition of an excess of acid to the preformed neutral ammonium or iminium salt. Thus the reaction between compound (II) and compound (III) has the ammonium or iminium salt in the same phase as said compounds.

The acid can be selected from the group consisting of acetic acid, trifluoroacetic acid, sulfuric acid, methanesulfonic acid or other alkylsulfonic acids, p-toluenesulfonic acid, dodecylbenzenesulfonic acid, camphorsulfonic acid, hydrochloric acid, phosphoric acid, and mixtures thereof; preferably the acid is selected from the group consisting of sulfuric acid, methanesulfonic acid, p-toluenesulfonic acid, dodecylbenzenesulfonic acid, and mixtures thereof; and more preferably from methanesulfonic acid, p-toluenesulfonic acid, dodecylbenzenesulfonic acid, and mixtures thereof.

The acid may be the same that forms the ammonium or iminium salt or may be a different one. Preferably it is the same acid. The excess of acid relative to the neutral ammonium or iminium salt is usually comprised between 10% and 300% molar, preferably between 30 mol % and 100 mol %, and still more preferably between 50 mol % and 80 mol %. That is, if the neutral ammonium salt formed by an amine and an acid is used in an amount which is 5 mol % with respect to the reagent of formula (III), the excess of acid is 8 mol %, which represents a 60 mol % excess over the neutral ammonium salt.

The ammonium or iminium salt can be supported on a solid substrate and thus it can be easily separated from the reaction medium. Said ammonium salt may be obtained by reaction of a primary, secondary or tertiary amine supported on a solid substrate and an acid or acid mixture and, in turn, the iminium salt may be the result of the reaction between the ammonium salt supported on the substrate and the compound of formula (II). The amine may be supported on multiple substrates such as, for example, silica gel, alumina, polystyrene or zeolite. Preferably the substrate is silica gel. Eventually such salts can be commercially available from Sigma-Aldrich or VWR, such, for example, benzylamine on polystyrene or silica gel functionalized with 3-(1-piperazino)propyl group. They can also be easily obtained by reacting an amine with a solid support functionalized with a good leaving group, such for example, chloromethyl resin supported on polystyrene.

Process

The process of the invention comprises reacting a compound of formula (II) with a compound of formula (III) in the presence of a catalytic amount of an ammonium or iminium salt in homogeneous phase.

The reaction may be carried out under atmospheric pressure at a temperature comprised between 70° C. and 145° C., preferably between 90° C. and 135° C., and more preferably between 110° C. and 130° C., and the reaction time is usually comprised between 30 minutes and 4 hours, preferably between 1 and 3 hours, and more preferably between 1 and 2 hours. The course of the reaction can be monitored by using techniques well known to the skilled in the art, such as, for example, gas chromatography or nuclear magnetic resonance.

The reaction is generally carried out in the absence of a solvent. However, if necessary a non-nucleophilic or weakly nucleophilic solvent can be added, such as, for example, pentane, heptane, cyclohexane, toluene, chloroform, ethyl acetate, butyrolactone, trifluoroethanol, and propylene carbonate.

Generally 1 equivalent of compound of formula (III), between 1 and 2.5 equivalents of compound of formula (II), preferably between 1.2 and 2 equivalents, and more preferably between 1.5 and 2 equivalents are used. Generally between 0.01 and 0.10 equivalents of amine, preferably between 0.02 and 0.08, more preferably between 0.025 and 0.06, and between 0.10 and 0.22 equivalents of acid, preferably between 0.12 and 0.16, and more preferably between 0.13 and 0.15 are used.

In the usual procedure the compound of formula (II) and the compound of formula (III) are placed in a reactor and the mixture is heated at a temperature comprised between 70° C. and 145° C., preferably between 110° C. and 130° C. Once reached this temperature, the catalytic amount of the preformed ammonium or iminium salt is added, or else the ammonium salt can by synthesized in situ in the reactor by reaction of the base and the corresponding acid. In the case of using a preformed ammonium or iminium salt it can be solubilized in the reaction medium by using an acid or a non-nucleophilic solvent as previously discussed.

The compound of formula (II) can be added preformed to the reaction, that is, it is isolated before carrying out the subsequent reaction with the compound of formula (III).

It can also be prepared in situ in the same reactor where the subsequent reaction with the compound (III) takes place and, in the context of the invention this embodiment is called tandem reaction. It has been observed that in both cases, the compound (II) preformed or formed in situ, the compound of formula (I) is obtained with the same degree of selectivity, where the degree of selectivity is the amount of monomer that has been produced with respect to what has reacted from compound (III). This degree of selectivity is very high and generally is greater than 90%.

In an alternative embodiment, the process for preparing the compound of formula (I) is characterized in that the compound of formula (II) is obtained in presence of the compound of formula (III) and a catalytic amount of an ammonium or iminium salt in homogeneous phase, from the reaction between formaldehyde gas or a source of formaldehyde, and a carboxylic acid anhydride, wherein in the compound of formula (II)

E is $(CH_2X)_m$, m is comprised between 1 and 20, preferably between 1 and 10, more preferably between 1 and 5, and still more preferably between 1 and 3,
X is O,
n=1,
F is:

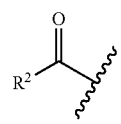

and
G is:

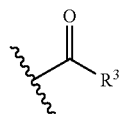

wherein $R^2$ and $R^3$ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety.

The source of formaldehyde can be, for example, paraformaldehyde or trioxane. The carboxylic acid anhydride may be, for example, acetic anhydride, propionic anhydride, benzoic acid anhydride, or acid anhydrides mixture.

In the context of the invention, this way of carrying out the process is called direct reaction. Thus, for example, a common way of carrying out this direct reaction involves placing in a reactor paraformaldehyde, acetic anhydride and butyl cyanoacetate at a temperature comprised between 120° C. and 130° C. in the presence of a catalyst prepared in situ in the same reactor from piperazine (5 mol %) and p-toluenesulfonic acid (15 mol %), or else with a 5 mol % of the neutral ammonium salt formed by piperazine and said acid, and an additional 5 mol % of acid for the reaction to take place in homogeneous phase. In this case the degree of selectivity is high, and is generally at least 70%.

In Table III different embodiments of the process of the invention are summarized, according to the way by which the compound of formula (II) and the ammonium or iminium salt are prepared, as well as the degree of selectivity that is usually obtained for each combination of conditions:

TABLE III

| Preparation of the compound of formula (II) | Preparation of the ammonium or iminium salt | Usual selectivity (%) |
|---|---|---|
| Preformed | In the same reactor | >90 |
| Tandem reaction | In the same reactor | >90 |
| Direct reaction | In the same reactor | >75 |
| Preformed | Preformed | >90 |
| Tandem reaction | Preformed | >90 |
| Direct reaction | Preformed | ca. 70 |

With respect to the preparation of the compound of formula (II), as indicated above:
- the term "Preformed" means that the compound of formula (II) has been prepared and isolated before being subjected to the reaction with the compound of formula (III);
- the expression "Tandem reaction" means that the compound of formula (II) is prepared in the same reactor in which the reaction with the compound of formula (III) takes place in the presence of a catalytic amount of the ammonium or iminium salt, and
- the expression "Direct reaction" refers to a specific embodiment of the preparation of the compound of formula (II) from formaldehyde or a source thereof and a carboxylic acid anhydride in the presence of the compound of formula (III) and a catalytic amount of the ammonium or iminium salt.

Regarding the preparation of the ammonium or iminium salt, as stated above:
- the expression "In the same reactor" means that the salt is prepared in situ in the same reactor in which takes place the reaction between the compound of formula (II) and the compound of formula (III); and
- the term "Preformed" means that the ammonium or iminium salt has been prepared and isolated.

In a preferred embodiment, during the process of the invention a stabilizing agent is introduced into the reaction mixture, said agent being selected from the group consisting of a free radical stabilizer and an acid stabilizer. Among the free radical stabilizers that can be employed are, for example, hydroquinone, pyrocatechol, resorcinol, or derivatives thereof, such as hydroquinone monoethyl ether, phenols such as di-t-butylphenol, 2,6-di-t-butyl-p-cresol, 2,2'-methylene-bis-(4-methyl-6-t-butylphenol), and dihydroxydiphenylmethane. Among the acid stabilizers are, for example, Lewis acids, sulfuric acid, hydrochloric acid, sulfonic acids, such as methanesulfonic acid, p-toluenesulfonic acid, or dodecylbenzenesulfonic (LAS), phosphoric acid, polyphosphoric acid, silylated esters of strong acids, such as derivatives of trialkylchlorosilanes, dialkyldichlorosilanes, alkyltrichlorosilanes, tetrachlorosilane with sulfonic acids, sulfuric acid or phosphoric acid.

The amount of stabilizing agent used to stabilize the compound of formula (I) prepared according to the process of the invention is well known to the skilled in the art, and can vary depending on the properties of the 1,1-disubstituted ethylene monomer.

The process of the invention has advantages over the processes described in the prior art because it allows the monomer to be prepared directly, avoiding the step of thermal depolymerization of a prepolymer, in this process simple, readily available and non-toxic starting products of well-defined structure are used, and it can be applied to a wide range of monomers: liquids with high boiling point, solids, monofunctional, multifunctional with the same group, multifunctional monomers with different groups, or specifically designed monomers, in high yield and purity after a final distillation in a standard industrial equipment. Furthermore, the reaction is carried out without the need of removing water or alcohols by azeotropic distillation; the catalytic system is not the source of the methylene group contained in the final monomer, so it is not necessary to use a stoichiometric amount thereof; the reaction takes place in an acidic or neutral medium which stabilizes the monomer once formed; the final product may be distilled directly from the reaction crude or may be precipitated if it is a solid; and a small amount of by-products is formed that can be easily recycled or removed.

Application Tests

The reactivity of the 1,1-disubstituted ethylene monomers obtained by the process of the invention can be assessed by measuring the time to fixture to bond different substrates using an adhesive prepared based on the these pure monomers.

In the Examples section, the procedure used is described in detail with three types of materials for testing the adhesive strength of said monomers: grit blasted mild steel, pine wood and polycarbonate as plastic material.

The monomers obtained with the process have high degree of purity and low content of acid, since in the three materials a time to fixture of less than or equal to 1 minute was obtained, depending on the material, and the complete polymerization in the presence of an initiator, it also was achieved in less than 1 min. It should be noted that the presence of acid delays the complete polymerization of the monomer in intimate contact with an initiator.

Thus, the 1,1-disubstituted ethylene monomers obtained by the process of the invention are appropriate for being used in the formulation of adhesive compositions.

The invention comprises the following embodiments:

1. Process for preparing 1,1-disubstituted ethylene monomers of general formula (I)

(I)

wherein:

A and D are independently selected from each other from the following functional groups CN, $CO_2R^1$, $COR^1$, $CONR^1_2$, $SO_2R^1$, $SO_3R^1$, $COPO(OR^1)_2$, $COPOR^1_2$, $NO_2$, wherein $R^1$ means a linear or branched, saturated or unsaturated $C_1$-$C_{20}$ alkyl, preferably linear, branched or alicyclic $C_1$-$C_3$ alkyl, or linear, branched or alicyclic $C_4$-$C_{20}$ alkyl, $C_1$-$C_{20}$ halogenated alkyl, $C_4$-$C_{20}$ alkyl silane, $C_1$-$C_{20}$ acetoxy silane, $C_2$-$C_{20}$ alkoxyalkyl, $C_2$-$C_{20}$ alkenyl, $C_2$-$C_{20}$ alkynyl, $C_2$-$C_{10}$ alkylene, $C_3$-$C_{20}$ cycloalkyl, alkylcycloalkyl, $C_3$-$C_{20}$ cycloalkenyl, alkylcycloalkenyl, aryl, substituted aryl, alkylaryl, substituted alkylaryl, aliphatic heterocyclic moiety, alkyl moiety linked to an aliphatic heterocycle, aromatic heterocycle moiety, alkyl moiety linked to an aromatic heterocycle, acrylic ester moiety, oxetane moiety, epoxy moiety, glycolate moiety, and carboxylic acid ester moiety;

which comprises the reaction of a compound of general formula (II)

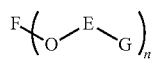
(II)

wherein:

E is $(CH_2X)_m$, m is comprised between 1 and 20,

X is O or S, when n=1, F is selected from the functional groups:

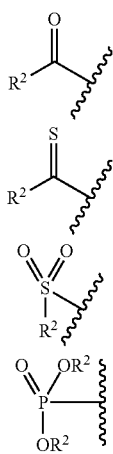

when n=2, F is selected from the functional groups:

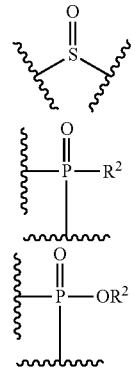

when n=3, F is:

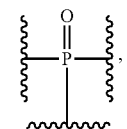

G is selected from the functional groups:

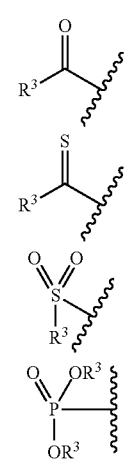

G and F are independently selected from each other, and $R^2$ and $R^3$ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, or when n=1, F may be connected to G through one $R^6$ group selected from $(CH_2)_p$, $(CHR')_p$, $(CR'R'')_p$, where p is comprised between 1-6, preferably between 1 and 4, and more preferably is 1, and R' and R'' may be the same or different $C_1$-$C_4$ alkyl groups, with a compound of general formula (III)

(III)

$A \diagdown D$ in the presence of a catalytic amount of an ammonium or iminium salt, wherein this salt is in homogeneous phase or supported on a solid substrate.

2.—Process according to embodiment 1, characterized in that the reaction between the compound of formula (II) and the compound of formula (III) is carried out in the presence of a catalytic amount of an ammonium or iminium salt in homogeneous phase.

3.—Process according to embodiments 1 or 2, characterized in that A and D are independently selected from each other from CN, $CO_2R^1$, and $COR^1$.

4.—Process according to embodiment 3, characterized in that A and D are independently selected from each other from CN and $COR^1$.

5.—Process according to any one of the embodiments 1 to 4, characterized in that $R^1$ means a linear or branched, saturated or unsaturated $C_1$-$C_{20}$ alkyl, preferably linear, branched or alicyclic $C_1$-$C_3$ alkyl, or linear, branched or alicyclic $C_4$-$C_{20}$ alkyl, $C_2$-$C_{20}$ alkoxyalkyl, $C_2$-$C_{10}$ alkylene, or acrylic ester moiety.

6.—Process according to any one of the embodiments 1 to 5, characterized in that in the compound of formula (II):

E is $(CH_2X)_m$, m is comprised between 1 and 5,

X is O, n=1,

F is selected from the functional groups:

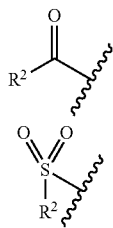

G is selected from the functional groups:

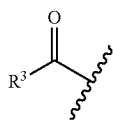

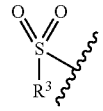

G and F are independently selected from each other, and $R^2$ and $R^3$ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety.

7.—Process according to embodiment 6, characterized in that in the compound of formula (II):

E is $(CH_2X)_m$, m is comprised between 1 and 3,

X is O, n=1,

F is:

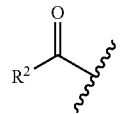

G is:

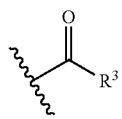

G and F are independently selected from each other, and $R^2$ and $R^3$ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety.

8.—Process according to embodiments 6 or 7, characterized in that $R^2$ and $R^3$ are independently selected from each other from the functional groups H and linear or branched $C_1$-$C_4$ alkyl.

9.—Process according to embodiment 8, characterized in that the compound of formula (II) is selected from the group consisting of methylene diacetate, oxybismethylene diacetate, methylene dipropionate and oxybismethylene dipropionate.

10.—Process according to embodiment 9, characterized in that the compound of formula (II) is methylene diacetate.

11.—Process according to any one of the embodiments 1 to 10, characterized in that the ammonium salt is the product resulting from the reaction of an acid with a primary, secondary or tertiary amine.

12.—Process according to embodiment 11, characterized in that the amine is selected from the group consisting of methylamine, piperazine, 2-methylpiperazine, N,N'-dimethoxymethylpiperazine, aniline, benzylamine, 2,6-difluorobenzylamine, trifluoroethylamine, and mixtures thereof.

13.—Process according to embodiment 12, characterized in that the amine is piperazine or 2-methylpiperazine.

14.—Process according to any one of the embodiments 1 to 10, characterized in that the iminium salt is an imine resulting from the reaction of a primary or secondary amine with an aldehyde or with a ketone, in neutral or acidic medium, and that contains an anion from an acid.

15.—Process according to embodiment 14, characterized in that the iminium salt is the result of the reaction of N,N-dimethylamine and formaldehyde.

16.—Process according to any one of the embodiments 11 to 15, characterized in that the acid is selected from the group consisting of acetic acid, trifluoroacetic acid, sulfuric acid, methanesulfonic acid, p-toluenesulfonic acid, dodecylbenzenesulfonic acid, camphorsulfonic acid, hydrochloric acid, phosphoric acid, and mixtures thereof.

17.—Process according to embodiment 16, characterized in that the acid is selected from methanesulfonic acid, p-toluenesulfonic acid, dodecylbenzenesulfonic acid, and mixtures thereof.

18.—Process according to the embodiments 11 or 14, characterized in that the ammonium or iminium salt is the salt formed between an amine selected from the group consisting of piperazine, N,N'-dimethoxymethylpiperazine, and 1,3,5-trimethylhexahydro-1,3,5-triazine, and an acid selected from methanesulfonic acid, p-toluenesulfonic acid, and dodecylbenzenesulfonic acid (LAS).

19.—Process according to embodiment 1, characterized in that the iminium salt is prepared by the reaction between a compound of general formula (II) and an ammonium salt resulting from the reaction between a primary, secondary or tertiary amine and an acid or an acid mixture.

20.—Process according to embodiment 19, characterized in that the amine is selected from N,N-dimethylamine, morpholine and N,N,N',N'-tetramethyldiamine methane, and the acid is selected from methanesulfonic acid, p-toluenesulfonic acid, dodecylbenzenesulfonic acid, and mixtures thereof.

21.—Process according to embodiment 20, characterized in that the secondary amine is N,N-dimethylamine and the acid is a mixture of p-toluenesulfonic acid and dodecylbenzenesulfonic acid.

22.—Process according to any one of the embodiments 1 to 21, characterized in that the ammonium or iminium salt is prepared in situ.

23.—Process according to any one of the embodiments 1 to 21, characterized in that a preformed ammonium or iminium salt is employed and an excess of acid is added relative to the neutral ammonium or iminium salt.

24.—Process according to any one of the embodiments 1 to 23, characterized in that the compound of formula (II) is isolated before carrying out the subsequent reaction with the compound of formula (III).

25.—Process according to any one of the embodiments 1 to 23, characterized in that the compound of formula (II) is prepared in situ in the same reactor where the subsequent reaction with the compound of formula (III) takes place.

26.—Process according to any one of the embodiments 1 to 23, characterized in that the compound of formula (II) is obtained in presence of the compound of formula (III) and a catalytic amount of an ammonium or iminium salt in homogeneous phase, from the reaction between formaldehyde gas or a source of formaldehyde, and a carboxylic acid anhydride, wherein in the compound of formula (II)

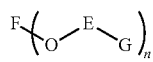
(II)

E is $(CH_2X)_m$, m is comprised between 1 and 20, preferably between 1 and 10, more preferably between 1 and 5, and still more preferably between 1 and 3,
X is O,
n=1,
F is:

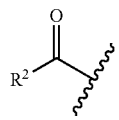

and
G is:

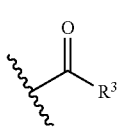

wherein $R^2$ and $R^3$ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety.

Next, several examples are provided which are illustrative of the invention but which are not limitative thereof.

EXAMPLES

Preparative Example 1: Preparation of Methylene Diacetate

In a 1 L double jacketed reactor 561 g (5.5 moles) of acetic anhydride and 158 g (5 moles) of paraformaldehyde of 95% purity were introduced and the suspension obtained was kept under stirring at room temperature until a homogeneous mixture was obtained. 2.45 g (0.025 moles) of concentrated sulfuric acid were added, while the oil in the reactor was heated to 160° C. When the temperature reached 138° C., paraformaldehyde was dissolved and the mixture became transparent. Once the temperature reached 160° C., a sample was taken and was analyzed by gas chromatography. The sampling was repeated every hour. After 3 hours of reaction, a conversion of 98% was observed, and the reaction mass was cooled down. The content of the reactor was transferred to another reactor and it was distilled. 671 g of a clear distillate of methylene diacetate was obtained, containing less than 1% of acetic anhydride, about 1% of oxybismethylene diacetate and 13.6% of acetic acid. This crude product was further purified by fractional distillation to yield methylene diacetate with a purity of approximately 100%.

Preparative Example 2: Preparation of the N,N-Dimethylmethylene Iminium D-Toluenesulfonate Salt by Anion Metathesis A mixture of 9.4 g (0.10 moles) of N,N-dimethylmethylene iminium (Sigma-Aldrich) and 18.6 g (0.10 moles) of molten methyl p-toluenesulfonate was heated to a temperature of about 100° C. under stirring in a 100 mL round-bottom flask equipped with a bubble counter. The flask was immersed in an oil bath at a temperature above 100° C. The reaction was quickly initiated and was accompanied by evolution of methyl chloride gas, which generated foam. The reaction time was 5 minutes, once the entire mass had melted.

The product was kept between 100-110° C. for another 30 minutes. After this period, it was introduced in a hermetically sealed plastic bottle where it solidified in the form of a very hard mass. The reaction yield was practically quantitative. The obtained product had a melting point of about 110° C.

Other salts were also prepared according to a substantially analogous process, such as, for example:
N,N-dimethylmethylene iminium benzenesulfonate, with a melting point of about 100° C.
N,N-dimethylmethylene iminium p-toluene/benzenesulfonate (mixture of anions), with a melting point of about 70° C.
N,N-dimethylmethylene iminium methanesulfonate, with a melting point of about 160° C.

The disclosed process is optimized from the method reported in V. P. Kukhar et al., Zhurnal Organicheskoi Khimii, 1981, 17 (1), 180-6.

This product was used in Example 10, included in Table VI below.

Preparative Example 3: Preparation of the Iminium Salt by Reaction of the Compound of General Formula (II) and an Ammonium Salt a) In a first step, the ammonium salt with a mixture of anions was prepared from N,N-dimethylamine according to the procedure described below.

Dodecylbenzenesulfonic acid (LAS), 238 g (0.8 moles) was rapidly added to a 1 L round bottom flask containing 306 g (1.2 moles) of an aqueous solution of p-toluenesulfonic acid 65% by weight (Stepanate p-TSA-LS, Stepan Europe). LAS was dissolved with a slight exothermia resulting in the formation of a clear, low viscosity solution. Immediately after the addition of LAS, an aqueous solution of 40% dimethylamine (236 g, 2.09 moles) was added over 5 min. The internal temperature of the reaction crude reached 80° C. at the end of the addition.

The still hot solution was transferred to a 2 L flask to remove water in the rotary evaporator the latter being equipped with a PTFE capillary tube. Initially, a 400-300 mbar vacuum was applied without air stream at 120° C., and then the vacuum was slowly reduced to 100 mbar. The neutral liquid dimethylammonium salt was finally dried at 30 mbar with a stream of air for 2 h at the temperature specified above. The yield was quantitative. The water content of the product was 0.085% as determined by Karl-Fisher analysis.

b) In a second step, the ammonium salt prepared according to the method described in step a) was reacted with methylene diacetate, obtained according to Preparative Example 1.

213 g of the dimethylammonium salt obtained in step a), containing 0.80 moles of amine nitrogen, and 47.8 g (0.16 moles) of non-purified LAS (Aldrich) were introduced in a 1 L flask.

Under stirring, 222 g (1.6 moles) of methylene diacetate were added to the mixture, and it was heated to an internal temperature of 100° C. At this temperature, samples of the reaction mixture were taken at 5 h, 7.5 h, 10 h and 12.5 h, and they were analyzed by magnetic resonance. Samples were concentrated in the rotary evaporator to remove the acetic acid produced during the reaction and also from methylene diacetate that could have remained unreacted. The analysis showed that within 5 h of reaction, a conversion of approximately 90% was obtained, being the yield equivalent to the conversion.

Preparative Example 4: Preparation of 1,4-diammoniocyclohexane di-p-toluenesulfonate A solution of p-toluenesulfonic acid monohydrate (22.04 g, 0.116 moles) in 20 mL of ethanol was added to a solution of piperazine (5 g, 0.058 moles) in 25 mL of ethanol. The reaction mixture was stirred at room temperature for 30 min. The solid obtained was filtered and washed with ethanol (3×20 mL). Afterwards, it was dried in the rotary evaporator to yield the ammonium salt quantitatively.

Comparative Example: Preparation of 2-Octyl Cyanoacrylate by Means of the Knoevenagel Reaction To a mixture of 42 g of paraformaldehyde (1.4 moles) in 100 mL of heptane, 0.54 g of piperidine (6 mmoles) were added in catalytic amounts and the resulting mixture was heated at 70° C. and kept at that temperature for 10 min. 250.8 g of 2-octyl cyanoacetate (1.2 moles) were added dropwise via an addition funnel over 30 minutes. The mixture was kept under reflux until no more water was collected. As a result of this reaction, the pre-polymer of 2-octyl cyanoacrylate was obtained.

Subsequently, phosphoric acid was added to the reaction mixture and then the solvent was removed by distillation. Next, the obtained residue was slowly neutralized with p-toluenesulfonic acid, and it was subjected to vacuum distillation to carry out the thermal depolymerization. The flask with the distillate was stabilized with a mixture of appropriate stabilizers, well known to the skilled in the art. The distillation was carried out at 1 mbar and 150° C., until the product began to distil. Afterwards, the temperature was increased to 200° C. until complete distillation of the monomer. Subsequent purifications of 2-octyl cyanoacrylate were carried out with vacuum distillation at 120° C. between 1-3 mbar. The yield of isolated pure monomer was 40%.

Example 1: Preparation of Butyl Cyanoacrylate (Compound of Formula (I) Wherein A is CN and D is —$CO_2$-n-Bu)

1.40 moles of butyl cyanoacetate and 2.1 moles of methylene diacetate, obtained through the preparative example 1, were added to a 1 L reactor. Subsequently, the mixture was heated to a temperature comprised between 120 and 130° C. Then 5 mol % of piperazine and 15 mol % of p-toluenesulfonic acid monohydrate were added. The reaction was monitored by gas chromatography or nuclear magnetic resonance every 30 min. After 1 hour, the reaction was terminated, and the n-butyl cyanoacrylate was obtained with a selectivity of 94%, where the selectivity is understood as the amount of monomer produced with respect to the cyanoacetate that has reacted. Subsequently, acetic acid was removed under vacuum and stabilizers were added to the residue for the distillation of the monomer.

Examples 2-6: Factorial Design Applied to the Preparation of Butyl Cyanoacrylate (Compound of Formula (I) Wherein A is CN and D is —$CO_2$-n-Bu)

n-butyl cyanoacrylate was selected as a model monomer to study the influence of the factors shown in Table IV on its synthesis, according to the process of the invention:

TABLE IV

| Factor | Low level | Medium level | High level |
| --- | --- | --- | --- |
| Methylene diacetate preparation | Preformed | Tandem reaction | Direct reaction |
| Ammonium or iminium salt preparation | In the same reactor | — | Preformed |

Following a procedure analogous to that of Example 1, Example 4 was prepared, in which the catalyst was previously synthesized according to Preparative Example 4. Thus, to a solution of butyl cyanoacetate (1.40 moles) and methylene diacetate (2.1 moles) at a temperature comprised between 120 and 130° C., 5 mol % of 1,4-diammoniocyclohexane di-p-toluenesulfonate was added together with additional 5 mol % of p-toluenesulfonic acid monohydrate in order to reach the same acidity as that described in Example 1.

In Examples 2 and 5, methylene diacetate was prepared according to a procedure analogous to that described in Preparative Example 1, being the reaction time of 2 hours. Subsequently, in both cases, butyl cyanoacetate (1.40 moles) was added over the same reaction crude, followed by a 5 mol % of piperazine and 10 mol % of p-toluenesulfonic acid monohydrate for Example 2, or a 5 mol % of the ammonium salt described in Preparative Example 4 for Example 5. From the addition of butyl cyanoacetate, the reaction was held under stirring at a temperature of 120° C. for 1 h.

In Examples 3 and 6 the process was performed by a direct reaction. In these examples, paraformaldehyde (2.1 moles), acetic anhydride (2.1 moles) and butyl cyanoacrylate (1.4 moles) were reacted together for 2 hours at a temperature comprised between 120 and 130° C. in the presence of the catalyst prepared in the same reactor from 5 mol % of piperazine and 15 mol % of p-toluenesulfonic acid for Example 3, or with a 5 mol % of the catalyst previously prepared and an additional 5 mol % of p-toluenesulfonic acid monohydrate for Example 6.

The combination of these factors and of the three levels for the preparation of methylene diacetate and of the two levels for the preparation of the ammonium or iminium salt was performed using a factorial design, as shown in Table V, where the selectivity obtained is also included:

TABLE V

| Example | Preparation of methylene diacetate | Preparation of the ammonium or iminium salt | Selectivity (%) |
|---|---|---|---|
| 1 | Preformed | In the same reactor | 94 |
| 2 | Tandem reaction | In the same reactor | 92 |
| 3 | Direct reaction | In the same reactor | 79 |
| 4 | Preformed | Preformed | 93 |
| 5 | Tandem reaction | Preformed | 96 |
| 6 | Direct reaction | Preformed | 70 |

It can be seen that the selectivity in obtaining of n-butyl cyanoacrylate is independent of the way of preparation of the catalyst, but the way of obtaining the compound of formula (II) has a certain influence, since it is high for a direct reaction, and very high for the previous preparation or through a tandem process.

Example 7: Preparation of Octadecyl Cyanoacrylate (Compound of Formula (I) Wherein A is CN and D is —$CO_2C_{18}H_{37}$)

84.3 g of octadecyl cyanoacetate were placed in a three necked flask of 250 mL with a thermometer, and 1.07 g of 1,3,5-trimethylhexahydro-1,3,5-triazine, 84.3 mg of 2,6-di-tert-butyl-4-methylphenol (BHT), and a mixture of 69.4 g of methylene diacetate and 13.4 g of dodecylbenzenesulfonic acid were added. The addition of the latter was carried out slowly to wet the solid cyanoacetate. The mixture was heated with gentle stirring to obtain a liquid mass. Then the reaction mass was kept at an internal temperature of 125° C. under rapid stirring until the signals of cyanoacetate in the nuclear magnetic resonance spectrum disappeared, between 1.5 and 2 h.

Once the reaction was finished, the crude was diluted with 50 g of glacial acetic acid, and cooled to room temperature while stirring slowly. Product crystallization started at a temperature of about 35° C. and the stirring continued at room temperature overnight. The solid was filtered, adding to the flask additional 35 g of acetic acid, and washing it three more times on the filter with 70 g of acetic acid at room temperature.

The wet product (127 g) was dissolved at 80° C. in 123 g of glacial acetic acid in the presence of 84 mg of BHT. The insoluble polymer fraction was removed, and the crystallization process was repeated at room temperature.

The crystals obtained were dried in a rotary evaporator at a slow speed at a temperature of 50° C. and applying a vacuum of 20 to 7 mbar to remove the acetic acid and to prevent product loss in the pump. After 1 h at 7 mbar, 61 g of 2-octadecyl cyanoacrylate were obtained, corresponding to a yield of 70%. The selectivity was 90%.

Example 8: Preparation of 1,6-Hexyl Biscyanoacrylate (Compound of Formula (I) Wherein A is CN and D is —$CO_2(CH_2)_6O_2C(CN)$=$CH_2$, Alkylene Moiety Linked to a Cyanoacrylic Ester)

A mixture of 59.4 g of methylene diacetate, 0.75 g of 2-methylpiperazine and 12.0 g of dodecylbenzenesulfonic acid was heated to 110° C. Then, 189 mg of 2,2-methylenebis(6-tert-butyl-4-methylphenol) were added, followed by 37.8 g of 1,6-hexanediol biscyanoacetate, which was slowly added in 30 portions over 30 min. The reaction was held at this temperature for 2 h, until the signals of cyanoacetate disappeared in the NMR spectrum.

The reaction mass was then concentrated in a rotary evaporator to remove the solvent (30 min at 80° C. and 10 mbar), and it was diluted with 45 g of toluene. The resulting solution contained no solids. To precipitate the product, 45 g of heptane were added dropwise during 30 min to the still hot toluene solution, and the resulting two phase mixture was cooled to room temperature with rapid stirring. Crystallization started approximately 20 min after the mixture had reached room temperature. The stirring was continued for additional 90 min until the liquid over the crystals was homogeneous, and the mixture was kept in the refrigerator overnight.

The solid product obtained was filtered, washed twice with 30 g of a cold mixture of toluene-heptane (1:1), which contained 30 ppm of boron trifluoride dibutyl etherate ($BF_3.Bu_2O$), and was vacuum dried for 2 h to obtain 29.6 g of 1,6-hexyl biscyanoacrylate, practically colourless, representing a yield of 71%. The selectivity was 90%, Example 9-35: Preparation of Cyanoacrylates of Formula (I)

Substantially following the process of the invention described in Example 1, the 1,1-disubstituted ethylene monomers listed in Table VI were prepared. This table shows the reaction time, the molar % of amine or imine, and the molar % of acid, as well as the selectivity obtained for each product:

TABLE VI

| Ex. | Monomer | Time | Mol % Base | Mol % Acid | Selectivity |
|---|---|---|---|---|---|
| 9 | n-butyl cyanoacrylate | 30 min | 5 $CH_3NH_2$ | 13 LAS | 64 |
| 10 | n-butyl cyanoacrylate | 2 h | 10 (tetramethylguanidinium cation) | 18 p-TSA | 87 |
| 11 | n-butyl cyanoacrylate | 30 min | 5 (aniline) | 13 LAS | 47 |
| 12 | n-butyl cyanoacrylate | 30 min | 5 (benzylamine) | 13 LAS | 60 |
| 13 | n-butyl cyanoacrylate | 30 min | 5 (2,6-difluorobenzylamine) | 13 LAS | 87 |
| 14 | n-butyl cyanoacrylate | 30 min | 5 $F_3C{-}NH_2$ | 13 LAS | 73 |
| 15 | n-butyl cyanoacrylate | 30 min | 5 $H_2N{-}NH_2$ (ethylenediamine) | 13 LAS | 49 |
| 16 | n-butyl cyanoacrylate | 30 min | 5 (tetrahydrofurfurylamine) | 13 LAS | 67 |
| 17 | n-butyl cyanoacrylate | 30 min | 5 (morpholine) | 13 LAS | 49 |

TABLE VI-continued

| Ex. | Monomer | Time | Mol % Base | Mol % Acid | Selectivity |
|---|---|---|---|---|---|
| 18 | 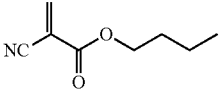 n-butyl cyanoacrylate | 30 min | 2.5 piperazine | 13 LAS | 75 |
| 19 | 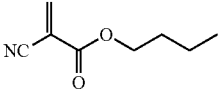 n-butyl cyanoacrylate | 1.5 h | 2.5 SiO2-propyl-piperazine | 13 LAS | 60 |
| 20 | 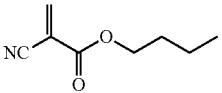 n-butyl cyanoacrylate | 30 min | 1.67 1,3,5-trimethyl-1,3,5-triazinane | 13 LAS | 65 |
| 21 | 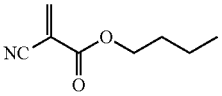 n-butyl cyanoacrylate | 30 min | 2.5 1,4-bis(methoxymethyl)piperazine | 13 LAS | 90 |
| 22 | 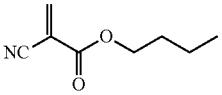 n-butyl cyanoacrylate | 1 h | 5 piperazine | 13 p-TSA | 87 |
| 23 | 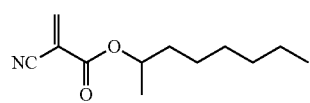 2-octyl cyanoacrylate | 2 h | 10 iminium | 18 LAS | 93 |
| 24 | 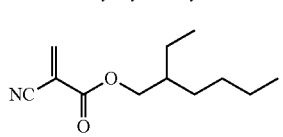 2-ethylhexyl cyanoacrylate | 2 h | 2.5 piperazine | 15 LAS | 92 |
| 25 | 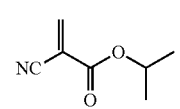 isopropyl cyanoacrylate | 2 h | 5 piperazine | 13 LAS | 96 |
| 26 | 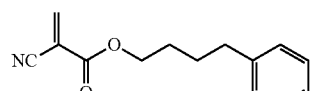 2-phenylethyl cyanoacrylate | 2 h | 2.5 piperazine | 15 LAS | 91 |

TABLE VI-continued

| Ex. | Monomer | Time | Mol % Base | Mol % Acid | Selectivity |
|---|---|---|---|---|---|
| 27 | cyclohexenylmethyl cyanoacrylate | 2 h | 2.5 piperazine | 15 LAS | 87 |
| 28 | menthyl cyanoacrylate | 1.5 h | 10 trimethylamine | 18 LAS | 95 |
| 29 | 2-methoxyethyl cyanoacrylate | 2 h | 5 piperazine | 15 LAS | 92 |
| 30 | 2-methoxyethyl cyanoacrylate | 2 h | 5 piperazine | 15 MSA | 96 |
| 31 | 2-ethoxyethyl cyanoacrylate | 2 h | 5 piperazine | 15 LAS | 91 |
| 32 | tetrahydrofurfuryl cyanoacrylate | 2 h | 2.5 piperazine | 15 LAS | 87 |
| 33 | 2-(2-methoxyethoxy)ethyl cyanoacrylate | 2 h | 10 trimethylamine | 18 LAS | 96 |
| 34 | trimethylsilylmethyl cyanoacrylate | 2 h | 2.5 2-methylpiperazine | 13 LAS | 96 |

TABLE VI-continued

| Ex. | Monomer | Time | Mol % Base | Mol % Acid | Selectivity |
|---|---|---|---|---|---|
| 35 | methylidene dimethylmalonate | 1.5 h | 10 H₃CO-CH₂CH₂-NH₂ | 13 LAS | 59 |

Wherein:
LAS: dodecylbenzenesulfonic acid
p-TSA: p-toluenesulfonic acid
MSA: methanesulfonic acid In Example 19 the base used was 3-(1-piperazino)propyl functionalized silica gel, with 0.8 mmoles/g loading (Sigma Aldrich) and dodecylbenzenesulfonic acid. Said reaction was also carried out following the process of the invention described in Example 1.

It can be seen that with the process of the invention a high selectivity is obtained in the preparation of the 1,1-disubstituted ethylene monomer.

Example 36: Comparison Between the Process of the Invention and the Knoevenagel Reaction Several cyanoacrylates have been prepared following the process described for the Knoevenagel reaction, and the yield obtained has been compared with that obtained using the method of the invention.

In Table VII the compounds prepared and the yield values for each process are shown:

TABLE VII

| Example | Ethylene monomer | Yield Process invention | Yield Knoevenagel |
|---|---|---|---|
| 7 | octadecyl cyanoacrylate | 70 | Not feasible |
| 8 | 1,6-hexanediol biscyanoacrylate | 71 | Not feasible |
| 23 | 2-octyl cyanoacrylate | 83 | 35-40 (40-45) (a) (b) |
| 24 | 2-ethylhexyl cyanoacrylate | 84 | ~60 (c) |
| 25 | isopropyl cyanoacrylate | 78 | 75 (65-70) (a) (c) |
| 26 | 2-phenylethyl cyanoacrylate | 78 | 39 (d) |
| 29 | 2-methoxyethyl cyanoacrylate | 76 | 45 (e) |
| 31 | 2-ethoxyethyl cyanoacrylate | 80 | 40 (e) |
| 32 | tetrahydrofurfuryl cyanoacrylate | 70 | 64 (35-40) (a) (f) |
| 34 | trimethylsilylmethyl cyanoacrylate | 66 | 30 (g) |

(a) Isolated yield obtained experimentally by reproducing the conditions disclosed in the literature.
(b) Holl etal., J. Microencapsulation, 2002, 19(6), 699.
(c) Holl etal., J. Microencapsulation, 2002, 19(6), 699.
(d) JP-A-06-192202
(e) Muzrahi et al., Acta Biomater., 2011, 7(8), 3150-3157
(f) U.S. Pat. No. 4,321,180
(g) EP-A-0127855

It can be seen that the yield obtained with the process of the invention is significantly superior to that obtained with the process according to the Knoevenagel reaction, and in some particular cases it has been possible the preparation of the monomer with a good yield, while it was not possible with the conditions of said reaction.

Example 37: Study of the Adhesive Properties of Monomers Obtained by the Process of the Invention The reactivity of 1,1-disubstituted ethylene monomers obtained by the process of the invention has been tested using as examples the alkoxyalkyl cyanoacrylates of Examples 30 and 31. To this end, the time to fixture needed to bond different substrates using an adhesive prepared from these pure monomers has been determined.

Three types of materials were used: grit blasted mild steel, pine wood and polycarbonate as plastic material.

To perform this test, the surface of the substrates was cleaned with isopropanol and then a droplet as small as possible of the pure monomer was applied to said substrate, afterwards an identical substrate was assembled over the first substrate and the assembly was held together, the bonding surface being 250 mm$^2$. The clamps were removed after a certain time, and a weight of 3 kg was suspended from one of the substrates, while the other was held in vertical position.

Time to fixture, expressed in seconds, is the time elapsed between the moment after assembling the two substrates with the monomer, and the moment when the sample can sustain a weight of 3 kg for 30 s without separating.

Indirectly, it was also assessed the total acid content present in the monomers due to the preparation process by observing the time required for the total curing of a standard sample in response to an initiator.

For this purpose an initiator was prepared as a solution of N-oxydiethylenebenzothiazole-2-sulfenamide in a non-nucleophilic solvent. An amount of said solution was added to the monomer and was thoroughly mixed. Subsequently, a narrow wooden stick of 2 mm of diameter was introduced into the mixture and was physically moved up and down with the hand until the mixture did not flow and stick was trapped in the polymerized adhesive. The time in which the complete polymerization occurs is indicative of the acid content of the monomer, since the initiator is neutralized with any acid present in the medium. The longer the time necessary to obtain the total polymerization, the higher is the acid content in the monomer.

In Table VIII the results for each type of material are shown, as well as the indirect assessment of acid content for the two indicated monomers:

The low times to fixture, of less than or equal to 1 min, depending on the substrate, and the low content of acid, with a time to complete polymerization of less than 1 min, illustrates the purity of the monomers prepared according to the process of the invention, and hence they are suitable for use in the formulation of adhesive compositions.

Example 38: Preparation of Ethyl Cyanoacrylate (Compound of Formula (I) Wherein A is CN and D is —CO$_2$-Et)

A mixture of 1.77 moles of ethyl cyanoacetate and 2.65 moles of methylene diacetate, obtained through the preparative example 1, was heated to a temperature comprised between 120 and 130° C. in 1 L reactor. Then, 2.5 mole % of piperazine and 13 mole % of methane sulfonic acid monohydrate. The reaction was monitored by gas chromatography or nuclear magnetic resonance every 30 min. After 2 hours, the reaction was considered terminated, and ethyl cyanoacrylate was obtained with a selectivity of 98%, where the selectivity is understood as the amount of monomer produced with respect to the cyanoacetate that has reacted. Then, acetic acid was removed under vacuum and stabilizers were added to the residue for the distillation of the monomer. The yield of ethyl cyanoacrylate was 82%.

Example 39: Preparation of 12-Methacryloyloxydodecyl Cyanoacrylate (Compound of Formula (I) Wherein A is CN and D is —CO$_2$R$^1$, Wherein R$^1$ is (CH$_2$)$_{12}$O$_2$C(Me)=CH$_2$, Acrylic Ester Moiety of Formula (IV) Wherein z=12, and R$^4$=Me)

A mixture of 25.3 g of 12-methacryloyloxydodecyl cyanoacetate, ca. 90% purity by gas chromatography assay, obtained for example according to the method disclosed in the British patent application GB-A-2311519, 19.8 g of methylene diacetate, obtained through the preparative example 1, 0.375 g of 2-methylpiperazine, 0.128 g of BHT, and 5.08 g of dodecylbenzenesulfonic acid (free from sulfuric acid) was brought to 120° C. and stirred at this temperature 45 min, the point when cyanoacetate signals checked by NMR had almost disappeared.

The reaction mass was then concentrated on rotatory evaporator to remove the solvent (30 min at 80° C. and 8 mbar), being obtained a brown oil, which did not contain any solid materials. That oil was twice extracted into 32 g

TABLE VIII

| | | Time to fixture | | | Indirect assessment of the acid content |
|---|---|---|---|---|---|
| Example | Monomer | Steel | Wood | Polycarbonate | |
| 30 | 2-methoxyethyl cyanoacrylate | 60 | 15-30 | 15 | 38-39 |
| 31 | 2-ethoxyethyl cyanoacrylate | 45 | 30 | 15 | 50-52 | portions of isooctane. The extracts were allowed to stand at room temperature in order to separate the catalyst as yellow paste. The product was precipitated by cooling at −20° C. The solid was filtrated and washed with 17.5 ml of freezing isooctane. Finally, 16.8 g of a slightly yellow waxy solid were obtained, which represented 64% yield. Selectivity was about 90%. The pure monomer was obtained by recrystallizing from low polar solvents like hexamethyldisiloxane or octane and the $^1$H-RMN spectrum showed clearly four vinyl protons associated with the two polymerisable functions: cyanoacrylate and methacrylate.

The invention claimed is:

1. Process for preparing 1,1-disubstituted ethylene monomers of general formula (I)

(I)

wherein:
A and D are independently selected from each other from the following functional groups: CN, $CO_2R^1$, $COR^1$, $CONR^1_2$, $SO_2R^1$, $SO_3R^1$, $COPO(OR^1)_2$, $COPOR^1_2$, $NO_2$, wherein $R^1$ is a linear or branched, saturated or unsaturated $C_1$-$C_{20}$ alkyl, $C_1$-$C_{20}$ halogenated alkyl, $C_4$-$C_{20}$ alkyl silane, $C_1$-$C_{20}$ acetoxy silane, $C_2$-$C_{20}$ alkoxyalkyl, $C_2$-$C_{20}$ alkenyl, $C_2$-$C_{20}$ alkynyl, $C_2$-$C_{10}$ alkylene, $C_3$-$C_{20}$ cycloalkyl, alkylcycloalkyl, $C_3$-$C_{20}$ cycloalkenyl, alkylcycloalkenyl, aryl, substituted aryl, alkylaryl, substituted alkylaryl, aliphatic heterocyclic moiety, alkyl moiety linked to an aliphatic heterocycle, aromatic heterocycle moiety, alkyl moiety linked to an aromatic heterocycle, acrylic ester moiety, oxetane moiety, epoxy moiety, glycolate moiety, and carboxylic acid ester moiety;

characterized in that it comprises the reaction of a compound of general formula (II)

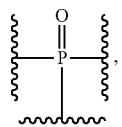

(II)

wherein:
E is $(CH_2X)_m$,
m is between 1 and 20,
X is O or S,
when n=1, F is selected from the functional groups:

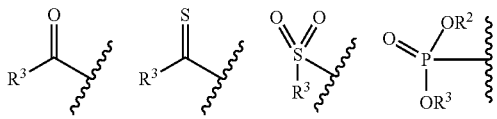

when n=2, F is selected from the functional groups:

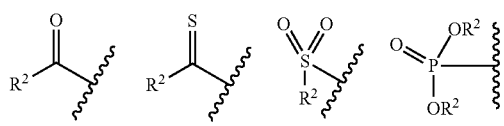

when n=3, F is:

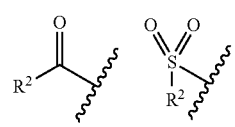

G is selected from the functional groups:

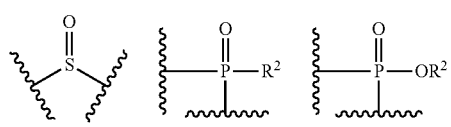

G and F are independently selected from each other, and
$R^2$ and $R^3$ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety, or
when n=1, F may be connected to G through one $R^6$ group selected from $(CH_2)_p$, $(CHR')_p$, $(CR'R'')_p$, where p is between 1-6, and R' and R'' may be the same or different $C_1$-$C_4$ alkyl groups, with a compound of general formula (III)

(III)

in the presence of a catalytic amount of an ammonium or iminium salt, wherein this salt is in homogeneous phase or supported on a solid substrate.

2. Process according to claim 1, wherein the reaction between the compound of formula (II) and the compound of formula (III) is carried out in the presence of a catalytic amount of an ammonium or iminium salt in homogeneous phase.

3. Process according to claim 1, wherein A and D are independently selected from each other from CN, $CO_2R^1$, and $COR^1$.

4. Process according to claim 1, wherein in the compound of formula (II):
E is $(CH_2X)_m$,
m is between 1 and 5,
X is O,
n=1,
F is selected from the functional groups:

G is selected from the functional groups:

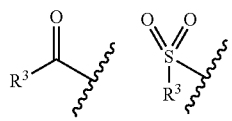

G and F are independently selected from each other, and $R^2$ and $R^3$ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety.

5. Process according to claim 4, wherein in the compound of formula (II):
E is $(CH_2X)_m$,
m is between 1 and 3,
X is O,
n=1,
F is:

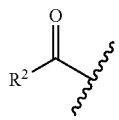

G is:

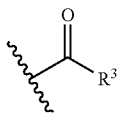

G and F are independently selected from each other, and $R^2$ and $R^3$ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety.

6. Process according to claim 5, wherein the compound of formula (II) is selected from the group consisting of methylene diacetate, oxybismethylene diacetate, methylene dipropionate and oxybismethylene dipropionate.

7. Process according to claim 1, wherein the ammonium salt is the product resulting from the reaction of an acid with a primary, secondary or tertiary amine.

8. Process according to claim 7, wherein the amine is selected from the group consisting of methylamine, piperazine, 2-methylpiperazine, N,N'-dimethoxymethylpiperazine, aniline, benzylamine, 2,6-difluorobenzylamine, trifluoroethylamine, and mixtures thereof.

9. Process according to claim 1, wherein the iminium salt is an imine resulting from the reaction of a primary or secondary amine with an aldehyde or with a ketone, in neutral or acidic medium, and that contains an anion from an acid.

10. Process according to claim 9, wherein the iminium salt is the result of the reaction of N, N-dimethylamine and formaldehyde.

11. Process according to claim 7, wherein the acid is selected from the group consisting of acetic acid, trifluoroacetic acid, sulfuric acid, methanesulfonic acid, p-toluenesulfonic acid, dodecylbenzenesulfonic acid, camphorsulfonic acid, hydrochloric acid, phosphoric acid, and mixtures thereof.

12. Process according to claim 1, wherein the iminium salt is prepared by the reaction between a compound of general formula (II) and an ammonium salt resulting from the reaction between a primary, secondary or tertiary amine and an acid or an acid mixture.

13. Process according to claim 1, wherein the ammonium or iminium salt is prepared in situ.

14. Process according to claim 1, wherein a preformed ammonium or iminium salt is employed and an excess of acid is added relative to the neutral ammonium or iminium salt.

15. Process according to claim 1, wherein the compound of formula (II) is obtained in presence of the compound of formula (III) and a catalytic amount of an ammonium or iminium salt in homogeneous phase, from the reaction between formaldehyde gas or a source of formaldehyde, and a carboxylic acid anhydride, wherein in the compound of formula (II)

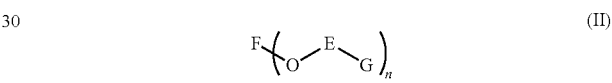 (II)

E is $(CH_2X)_m$, m is between 1 and 20,
X is O,
n=1,
F is:

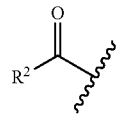

and
G is:

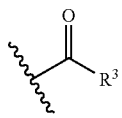

wherein $R^2$ and $R^3$ are independently selected from each other from the functional groups H, linear or branched $C_1$-$C_4$ alkyl, linear or branched $C_1$-$C_4$ halogenated alkyl, carboxy substituted $C_1$-$C_4$ alkyl, $C_3$-$C_{10}$ cycloalkyl, optionally substituted aryl, and a heterocyclic moiety.

* * * * *